(12) United States Patent
Haus et al.

(10) Patent No.: US 11,730,572 B2
(45) Date of Patent: Aug. 22, 2023

(54) APPARATUS FOR ATTACHING A DENTAL COMPONENT TO A DENTAL IMPLANT

(71) Applicant: NOBEL BIOCARE SERVICES AG, Kloten (CH)

(72) Inventors: Adrian Haus, Zürich (CH); Lars Jörneus, Frillesås (SE); Thomas Fischer, Rapperswil (CH); Thomas Eriksson, Gothenburg (SE); Mikael Brunell, Mariefred (SE)

(73) Assignee: Nobel Biocare Services AG, Kloten (CH)

( * ) Notice: Subject to any disclaimer, the term of this patent is extended or adjusted under 35 U.S.C. 154(b) by 0 days.

(21) Appl. No.: 16/165,320

(22) Filed: Oct. 19, 2018

(65) Prior Publication Data

US 2019/0117346 A1    Apr. 25, 2019

Related U.S. Application Data

(63) Continuation of application No. 14/108,712, filed on Dec. 17, 2013, now Pat. No. 10,149,741.

(30) Foreign Application Priority Data

Dec. 21, 2012 (GB) .................................. 1223210.4

(51) Int. Cl.
*A61C 8/00* (2006.01)
*A61K 6/802* (2020.01)

(52) U.S. Cl.
CPC .......... *A61C 8/0068* (2013.01); *A61C 8/0066* (2013.01); *A61K 6/802* (2020.01)

(58) Field of Classification Search
CPC ...... A61C 8/0066; A61C 8/0068; A61K 6/802
See application file for complete search history.

(56) References Cited

U.S. PATENT DOCUMENTS

| | | | |
|---|---|---|---|
| 2,721,387 | A | 10/1955 | Ashuckian |
| 4,259,072 | A | 3/1981 | Hirabayashi et al. |
| 4,560,353 | A | 12/1985 | Schulte et al. |
| 4,575,340 | A | 3/1986 | Lustig |
| 4,746,293 | A | 5/1988 | Lundgren et al. |
| 4,758,161 | A | 7/1988 | Niznick |
| 4,763,788 | A | 8/1988 | Jörneus et al. |

(Continued)

FOREIGN PATENT DOCUMENTS

| | | |
|---|---|---|
| AU | A-75458/96 | 6/1997 |
| CH | 692 542 | 7/2002 |

(Continued)

OTHER PUBLICATIONS

Brodbeck, Urs, "The ZiReal Post: A New Ceramic Implant Abutment," J Esthet Restor Dent 15:10-24, 2003.

(Continued)

*Primary Examiner* — Nicholas D Lucchesi
*Assistant Examiner* — Hao D Mai
(74) *Attorney, Agent, or Firm* — Knobbe, Martens, Olson & Bear, LLP

(57) ABSTRACT

The present disclosure relates to an apparatus of attaching a dental component having an angulated screw channel to a dental implant. The present disclosure also relates to a dental component having an angulated screw channel and a metal adapter.

9 Claims, 3 Drawing Sheets

(56) References Cited

U.S. PATENT DOCUMENTS

| | | | |
|---|---|---|---|
| 4,824,372 A | 4/1989 | Jörnéus et al. |
| 4,846,683 A | 7/1989 | Lazzara et al. |
| 4,850,870 A | 7/1989 | Lazzara et al. |
| 4,850,873 A | 7/1989 | Lazzara et al. |
| 4,854,872 A | 8/1989 | Detsch |
| 4,856,994 A | 8/1989 | Lazzara et al. |
| 4,872,839 A | 10/1989 | Brajnovic |
| 4,904,187 A | 2/1990 | Zingheim |
| 4,955,811 A | 9/1990 | Lazzara et al. |
| 4,988,297 A | 1/1991 | Lazzara et al. |
| 4,988,298 A | 1/1991 | Lazzara et al. |
| 5,000,686 A | 3/1991 | Lazzara et al. |
| 5,006,069 A | 4/1991 | Lazzara et al. |
| 5,015,186 A | 5/1991 | Detsch |
| 5,022,860 A | 6/1991 | Lazzara et al. |
| 5,030,096 A | 7/1991 | Hurson et al. |
| 5,035,619 A | 7/1991 | Daftary |
| 5,040,982 A | 8/1991 | Stefan-Dogar |
| 5,040,983 A | 8/1991 | Binon |
| 5,064,373 A | 11/1991 | Staubli et al. |
| 5,064,375 A | 11/1991 | Jörnéus |
| 5,069,622 A | 12/1991 | Rangert et al. |
| 5,071,345 A | 12/1991 | Rosen |
| 5,071,351 A | 12/1991 | Green, Jr. et al. |
| 5,073,111 A | 12/1991 | Daftary |
| 5,082,442 A | 1/1992 | Rosen |
| 5,087,200 A | 2/1992 | Brajnovic et al. |
| 5,100,323 A | 3/1992 | Friedman et al. |
| 5,105,690 A | 4/1992 | Lazzara et al. |
| 5,106,300 A | 4/1992 | Voitik |
| 5,125,839 A | 6/1992 | Ingber et al. |
| 5,125,841 A | 6/1992 | Carlsson et al. |
| 5,135,395 A | 8/1992 | Marlin |
| 5,145,371 A | 9/1992 | Jörnéus |
| 5,145,372 A | 9/1992 | Daftary et al. |
| 5,152,687 A | 10/1992 | Amino |
| 5,154,612 A | 10/1992 | Carlsson et al. |
| 5,169,309 A | 12/1992 | Staubli et al. |
| 5,188,800 A | 2/1993 | Green, Jr. et al. |
| 5,209,659 A | 5/1993 | Friedman et al. |
| 5,209,666 A | 5/1993 | Balfour et al. |
| 5,213,502 A | 5/1993 | Daftary |
| 5,238,405 A | 8/1993 | Marlin |
| 5,246,370 A | 9/1993 | Caotoam |
| 5,259,759 A | 11/1993 | Jörnéus et al. |
| 5,269,685 A | 12/1993 | Jörnéus et al. |
| 5,281,140 A | 1/1994 | Niznick |
| 5,282,746 A | 2/1994 | Sellers et al. |
| 5,292,252 A | 3/1994 | Nickerson et al. |
| 5,297,963 A | 3/1994 | Daftary |
| 5,316,476 A | 5/1994 | Krauser |
| 5,334,024 A | 8/1994 | Niznick |
| 5,336,090 A | 8/1994 | Wilson, Jr. et al. |
| 5,338,196 A | 8/1994 | Beaty et al. |
| 5,344,457 A | 9/1994 | Pilliar et al. |
| 5,350,302 A | 9/1994 | Marlin |
| 5,368,483 A | 11/1994 | Sutter et al. |
| 5,417,568 A | 5/1995 | Giglio |
| 5,419,702 A | 5/1995 | Beaty et al. |
| 5,431,567 A | 7/1995 | Daftary |
| 5,439,380 A | 8/1995 | Marlin |
| 5,447,435 A | 9/1995 | Brodbeck |
| 5,476,383 A | 12/1995 | Beaty et al. |
| 5,492,471 A | 2/1996 | Singer |
| 5,564,921 A | 10/1996 | Marlin |
| 5,584,694 A | 12/1996 | Forsmalm et al. |
| 5,658,147 A | 8/1997 | Phimmasone |
| 5,662,474 A | 9/1997 | Jörnéus et al. |
| 5,685,714 A | 11/1997 | Beaty et al. |
| 5,702,252 A | 12/1997 | Rogers et al. |
| 5,725,375 A | 3/1998 | Rogers |
| 5,741,267 A | 4/1998 | Jörnéus et al. |
| 5,829,977 A | 11/1998 | Rogers et al. |
| 5,873,720 A | 2/1999 | Jörnéus et al. |
| 5,873,722 A | 2/1999 | Lazzara et al. |
| RE36,126 E | 3/1999 | Beaty et al. |
| 5,904,483 A | 5/1999 | Wade |
| 5,934,906 A | 8/1999 | Phimmasone |
| 5,947,732 A | 9/1999 | Beaty et al. |
| 5,947,733 A * | 9/1999 | Sutter ............... A61C 8/005 433/173 |
| 5,989,026 A | 11/1999 | Rogers et al. |
| 6,012,923 A | 1/2000 | Bassett et al. |
| 6,048,203 A | 4/2000 | Rosenberg |
| RE36,689 E | 5/2000 | Beaty et al. |
| 6,068,479 A | 5/2000 | Kwan |
| 6,152,737 A | 11/2000 | Beaty et al. |
| 6,159,008 A | 12/2000 | Kumar |
| 6,168,435 B1 | 1/2001 | Beaty et al. |
| 6,174,166 B1 | 1/2001 | Jörnéus |
| 6,196,842 B1 | 3/2001 | Jörnéus |
| 6,227,856 B1 | 5/2001 | Beaty et al. |
| RE37,227 E | 6/2001 | Brodbeck |
| 6,276,938 B1 | 8/2001 | Jörnéus et al. |
| 6,290,499 B1 | 9/2001 | Lazzara et al. |
| 6,343,930 B1 | 2/2002 | Beaty et al. |
| 6,358,050 B1 | 3/2002 | Bergstrom et al. |
| 6,382,977 B1 | 5/2002 | Kumar |
| 6,394,806 B1 | 5/2002 | Kumar |
| 6,394,809 B2 | 5/2002 | Rogers et al. |
| 6,419,489 B1 | 7/2002 | Jörnéus et al. |
| 6,561,805 B2 | 5/2003 | Kumar |
| 6,626,911 B1 | 9/2003 | Engman et al. |
| 6,644,969 B2 | 11/2003 | Kumar |
| 6,655,962 B1 | 12/2003 | Kennard |
| 6,769,913 B2 | 8/2004 | Hurson |
| 6,827,575 B1 | 12/2004 | Jörnéus |
| 6,848,908 B2 | 2/2005 | Björn et al. |
| 6,896,517 B1 | 5/2005 | Björn et al. |
| 6,902,401 B2 | 6/2005 | Jörnéus et al. |
| 7,008,228 B2 | 3/2006 | Björn et al. |
| 7,338,286 B2 | 3/2008 | Porter et al. |
| 7,363,239 B1 | 4/2008 | Andersson et al. |
| 7,484,959 B2 | 2/2009 | Porter et al. |
| 7,491,058 B2 | 2/2009 | Jörnéus et al. |
| 7,665,989 B2 | 2/2010 | Brajnovic et al. |
| 8,038,445 B2 | 10/2011 | Brajniov et al. |
| 8,231,825 B2 | 7/2012 | Eriksson et al. |
| 8,272,871 B2 | 9/2012 | Hurson |
| 8,608,473 B2 | 12/2013 | Kennard |
| 8,805,658 B2 | 8/2014 | Pettersson et al. |
| 8,915,735 B1 | 12/2014 | Carlsson et al. |
| 9,125,708 B2 | 9/2015 | Carvalho et al. |
| 2002/0192620 A1 | 12/2002 | Jörnéus et al. |
| 2003/0104336 A1 | 6/2003 | Sethi et al. |
| 2003/0124488 A1 | 7/2003 | Gittleman |
| 2003/0162149 A1 | 8/2003 | Björn et al. |
| 2005/0019731 A1 | 1/2005 | Björn et al. |
| 2005/0065525 A1 | 3/2005 | Aringskog et al. |
| 2006/0008772 A1 | 1/2006 | Brajnovic et al. |
| 2006/0110706 A1 | 5/2006 | Jörnéus et al. |
| 2006/0246396 A1 | 11/2006 | Suttin et al. |
| 2007/0117066 A1 | 5/2007 | Jörnéus et al. |
| 2007/0281278 A1 | 12/2007 | Jörnéus et al. |
| 2008/0102420 A1 | 5/2008 | Porter et al. |
| 2008/0166682 A1 | 7/2008 | Björn et al. |
| 2008/0311544 A1 * | 12/2008 | Lee ............... A61C 8/0089 433/141 |
| 2009/0081612 A1 | 3/2009 | Jörnéus et al. |
| 2009/0130629 A1 | 5/2009 | Towse et al. |
| 2009/0136899 A1 | 5/2009 | Porter et al. |
| 2009/0239200 A1 | 9/2009 | Brajnovic et al. |
| 2009/0298013 A1 | 12/2009 | Baruc |
| 2010/0291509 A1 | 11/2010 | Berggren et al. |
| 2010/0297583 A1 | 11/2010 | Benzon et al. |
| 2010/0323327 A1 | 12/2010 | Eriksson et al. |
| 2011/0014586 A1 | 1/2011 | Jörnéus et al. |
| 2011/0060558 A1 | 3/2011 | Pettersson et al. |
| 2011/0123948 A1 | 5/2011 | Hinrichsen |
| 2011/0123953 A1 | 5/2011 | Jörnéus et al. |
| 2011/0183291 A1 | 7/2011 | Malo Carvalho et al. |
| 2011/0217675 A1 * | 9/2011 | Farre Berga ........... A61C 8/005 433/172 |
| 2012/0009545 A1 | 1/2012 | Eriksson et al. |

(56) References Cited

U.S. PATENT DOCUMENTS

| | | | |
|---|---|---|---|
| 2012/0077150 A1 | 3/2012 | Goodman et al. | |
| 2012/0191097 A1 | 7/2012 | Jörnéus et al. | |
| 2012/0191103 A1 | 7/2012 | Jörnéus et al. | |
| 2012/0246916 A1* | 10/2012 | Farre Berga | A61C 8/0068 29/700 |
| 2012/0295224 A1 | 11/2012 | Jörnéus et al. | |
| 2012/0301850 A1 | 11/2012 | Sollberger et al. | |
| 2012/0326343 A1 | 12/2012 | Eriksson et al. | |
| 2013/0045463 A1 | 2/2013 | Lindstrom et al. | |
| 2014/0011160 A1 | 1/2014 | Jörnéus et al. | |
| 2014/0124374 A1 | 5/2014 | Eriksson et al. | |
| 2014/0186797 A1 | 7/2014 | Haus | |
| 2014/0349250 A1* | 11/2014 | Elsner | A61C 8/0051 433/174 |
| 2015/0230890 A1 | 8/2015 | Malo Carvalho et al. | |

FOREIGN PATENT DOCUMENTS

| | | | |
|---|---|---|---|
| DE | 21 57 139 | 5/1972 | |
| DE | 27 17 506 | 5/1978 | |
| DE | 32 24 112 | 2/1984 | |
| DE | 34 44 780 | 6/1986 | |
| DE | 38 25 601 | 3/1989 | |
| DE | 41 27 839 | 3/1992 | |
| DE | 42 30 009 | 1/1993 | |
| DE | 101 29 684 A1 | 1/2003 | |
| DE | 10 2009 057754 A1 | 6/2011 | |
| EP | 0 377 068 B1 | 11/1992 | |
| EP | 0 534 078 A1 | 3/1993 | |
| EP | 0 320 024 B1 | 12/1993 | |
| EP | 0 474 571 B1 | 4/1995 | |
| EP | 0 477 644 B1 | 5/1996 | |
| EP | 0 657 146 B1 | 4/1998 | |
| EP | 1 269 932 A1 | 1/2003 | |
| EP | 1 073 381 B1 | 9/2004 | |
| EP | 0 786 966 B1 | 5/2006 | |
| EP | 0 837 658 B1 | 4/2007 | |
| EP | 1 021 997 B1 | 5/2007 | |
| EP | 1 124 501 B1 | 6/2007 | |
| EP | 2 025 302 A1 | 2/2009 | |
| EP | 2 090 263 A1 | 8/2009 | |
| EP | 2 127 612 A1 | 12/2009 | |
| EP | 1 613 237 B1 | 2/2011 | |
| EP | 1 419 746 B1 | 6/2011 | |
| EP | 1 820 467 B1 | 7/2015 | |
| GB | 2 213 065 | 8/1989 | |
| GB | 2 487 553 | 8/2012 | |
| SU | 1 570 720 | 6/1990 | |
| WO | WO 93/02632 | 2/1993 | |
| WO | WO 097/10770 | 3/1997 | |
| WO | WO 00/24335 | 5/2000 | |
| WO | WO 03/049636 | 6/2003 | |
| WO | WO 2004/002358 | 1/2004 | |
| WO | WO 2008/128757 | 10/2008 | |
| WO | WO-2013050796 A1 * | 4/2013 | A61C 13/0004 |
| WO | WO 2014/095033 | 6/2014 | |
| WO | WO 2014/095034 | 6/2014 | |

OTHER PUBLICATIONS

International Search Report for Application No. PCT/EP2013/003806 dated Mar. 19, 2014 in 4 pages [the ISR for the PCT Application of U.S. Appl. No. 14/654,440].

International Search Report for Application No. PCT/EP2013/003807 dated Apr. 9, 2014 in 5 pages [the ISR for the PCT Application of U.S. Appl. No. 14/654,407].

* cited by examiner

APPARATUS FOR ATTACHING A DENTAL COMPONENT TO A DENTAL IMPLANT

CROSS-REFERENCE TO RELATED APPLICATIONS

This application is a continuation of U.S. patent application Ser. No. 14/108,712, filed Dec. 17, 2013, which claims priority benefit of GB Patent Application No. 1223210.4, filed on Dec. 21, 2012. The disclosures of the prior applications are incorporated by reference herein in their entireties and should be considered a part of this application.

The present invention relates to a method of attaching a dental component to a dental implant. The present invention also relates to a dental component for attachment to a dental implant.

WO2004002358 A1 discloses a ceramic spacer with associated adapter designed to be fitted on an implant. The adapter comprises first and second portions designed to cooperate with the spacer and the implant, respectively, for securing the spacer on the implant.

Typically, to attach a spacer of the type disclosed in WO2004002358 A1 to the dental implant, the adapter is first attached to the spacer. The adapter/spacer is then applied to the implant. Thereafter, a screw is inserted through the spacer and used to fix the spacer to the implant. However, this method may not be optimal for all types of spacers.

The present inventors have realized that in case the spacer is provided with an angulated screw channel, the method described above may not be optimal, since the angulated screw channel then may need a long straight portion to accommodate the screw aligned with the dental implant before it is screwed into the implant.

The present invention is defined in the appended independent claims. Embodiments are defined in the appended dependent claims.

According to an aspect of the present invention, there is provided a method of attaching a dental component to a dental implant, the dental component comprising: a component body, wherein the component body comprises a screw channel passing through the component body and forming a first opening at a first end and a second opening at an apical end, and a screw seat proximal to the apical end of the screw channel for seating the head of a screw for the fixation of the dental component to the dental implant, wherein the longitudinal axis of the screw channel at the first end does not match the longitudinal axis of the screw channel at the apical end; and a metal adapter attachable to the component body, wherein the metal adapter comprises a bore passing through the metal adapter and forming a coronal opening and an apical opening, which method comprises: providing the component body without the metal adapter; inserting the screw into the screw channel through the first opening, and passing the screw through the screw channel so that a portion of the screw opposite said head protrudes through the second opening at the apical end of the screw channel; attaching the metal adapter to the component body as said portion of the screw protrudes through the second opening; and attaching the component body with the attached metal adapter to the dental implant, and fixing the component body with the attached metal adapter to the dental implant using the screw.

By changing the order in which the component body, the metal adapter, the implant and the screw are manipulated, the angulated screw channel in the component body can be made narrower.

The head of the screw may be seated on the screw seat as said portion of the screw protrudes through the second opening.

The metal adapter may be adapted to be attached to the apical end of the component body, wherein the bore of the metal adapter is aligned with the screw channel at the second opening when the metal adapter is attached to the component body.

The metal adapter may have a conical connection interface for attachment to the dental implant, wherein the conical connection interface includes an external conical shape tapering towards the apical end of the metal adapter, and an external indexed portion provided apically of the conical shape adjacent to the apical end of the metal adapter. Alternatively, the metal adapter includes at least one convex lobe adapted to abut against at least one corresponding concave recess in the component body for preventing rotation between the component body and the metal adapter, wherein said at least one convex lobe extends apically of an apical end of the component body when the metal adapter is attached to the component body.

The metal adapter may be removably attachable to the component body, for example by means of friction-fit and/or snap-locking.

The metal adapter may comprise at least one flexible arm with a protrusion adapted to press against a side wall and/or snap into any corresponding undercut of the component body for securing the metal adapter to the component body in the coronal-apical direction.

The component body is adapted to support a dental restoration.

The component body may be a full-contour part.

The component body may be ceramic.

The dental implant may be arranged in a physical model, wherein the dental implant optionally is a replica.

The dental implant may be anchored in a jaw bone of a patient.

According to another aspect of the present invention, there is provided a dental component for attachment to a dental implant, the dental component comprising: a ceramic component body, wherein the component body comprises a screw channel passing through the component body and forming a first opening at a first end and a second opening at an apical end, and a screw seat proximal to the apical end of the screw channel for seating the head of a screw for the fixation of the dental component to the dental implant, wherein the longitudinal axis of the screw channel at the first end does not match the longitudinal axis of the screw channel at the apical end; and a metal adapter removably attachable to the component body, wherein the metal adapter comprises a bore passing through the metal adapter and forming a coronal opening and an apical opening. This aspect may exhibit the same or similar features and/or technical effects as the previously discussed aspects, and vice versa.

According to yet another aspect of the present invention, the dental component is provided in combination with the dental implant.

These and other aspects of the present invention will now be described in more detail, with reference to the appended drawings showing currently preferred embodiments of the invention.

FIGS. 1a-1e show a method of attaching a dental component 10, for example an abutment, with an angulated screw channel 60 to a dental implant 46.

Figure 2:
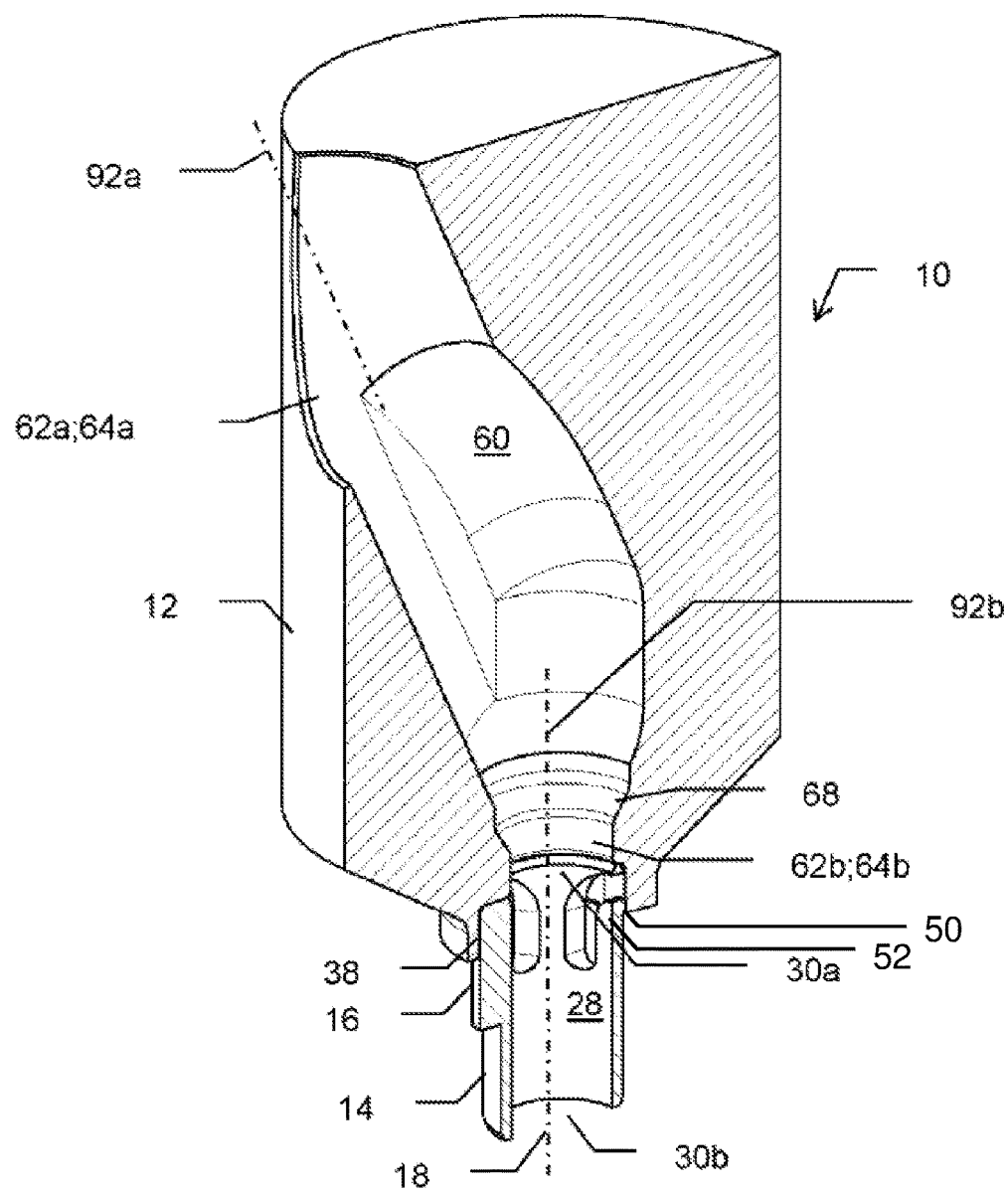
FIG. 2 is a cross-sectional view of a dental component according to an embodiment of the present invention.

The dental component 10 comprises a coronal component body 12, see also FIG. 2. The outer shape of the component body 12 in the figures may be schematic. The component body 12 may be adapted to support a dental restoration or a dental prosthesis, such as a single-unit restoration (crown) or a bridge. The restoration or prosthesis may for example be cemented to the component body 12. Alternatively, the dental component itself may be a crown or bridge. Also, the component body of the present dental component may be a full-contour part. The component body 12 is preferably made entirely of ceramic material such as zirconia.

The dental component 10 further comprises an apical metal adapter 14. The metal adapter 14 is for example made of titanium or titanium alloy. As in the illustrated embodiment, the metal adapter 14 may include at least one convex lobe 16 adapted to abut against at least one corresponding concave recess 38 in the component body 12 for preventing rotation between the component body 12 and the metal adapter 14. The at least one convex lobe 16 extends apically of an apical end 34 of the component body 12 when the metal adapter 14 is properly attached to the component body 12, whereby at least one convex lobe 16 also abut can against at least one corresponding concave recess 44 in the dental implant 46 for preventing rotation between the dental component 10 and the dental implant 46. Alternatively, the metal adapter may have a conical connection interface (not shown) for attachment to a dental implant. The conical connection interface may include an external conical shape tapering towards the apical end of the metal adapter, and an external indexed portion provided apically of the conical shape at the apical end of the metal adapter.

The metal adapter 14 further comprises a central bore 28. The bore 28 passes through the metal adapter 14, and forms a coronal opening 30a and an apical opening 30b.

The metal adapter 14 is preferably removably attachable to the component body 12, e.g. by means of friction-fit and/or snap-locking. Other options include press-fit and surface roughness, but not gluing. In this way, the metal adapter 12 may repeatedly be attached/detached. The metal adapter 12 may comprise at least one flexible arm 52 with a protrusion 50 is adapted to press against a side wall 44 and/or snap into any corresponding undercut or recess (not shown) of the component body 12 when the metal adapter 14 is attached to the component body 12, for preventing displacement between the metal adapter 14 and the component body 12 in the coronal-apical direction.

The component body 12 further comprises a screw channel 60. The screw channel 60 passes through the component body 12, and forms a first opening 62a at a first end 64a of the screw channel 60 and a second opening 62b at a second (apical) end 64b of the screw channel 60. The longitudinal axis 92a of the screw channel 60 at the first end 64a does not match the longitudinal axis 92b of the screw channel 60 at the second end 64b. That is, the screw channel 60 is angulated. The longitudinal axis 92b of the screw channel 60 at the second end 64b is aligned with the overall longitudinal axis 18 of the dental component 10. The first opening 64a is situated at one of the sides of the component body 12.

In the screw channel 60, there is provided a screw seat 68 proximal to the second end 64b. The screw channel 60 preferably includes an inclined surface defining said screw seat 68. The screw seat 68 is adapted to seat the head 70 of a screw 72 used for fixing the dental component 10 to the dental implant 46. Opposite the head 70, the screw 72 has an external thread 74. Also, when the component body 12 and the metal adapter 14 are assembled, the screw channel 60 of the component body 12 and the bore 28 of the metal adapter 14 are aligned.

The component body and metal adapter are also described in Applicant's co-pending applications entitled "ABUTMENT AND METHOD OF ATTACHING AN ABUTMENT TO A DENTAL IMPLANT" and "DENTAL COMPONENT WITH METAL ADAPTER", the contents of which herein are incorporated by reference.

Returning to FIGS. 1a-1e, first the component body 12 with the angulated screw channel 60 is provided without the metal adapter 14 (FIG. 1a).

Figure 1B:
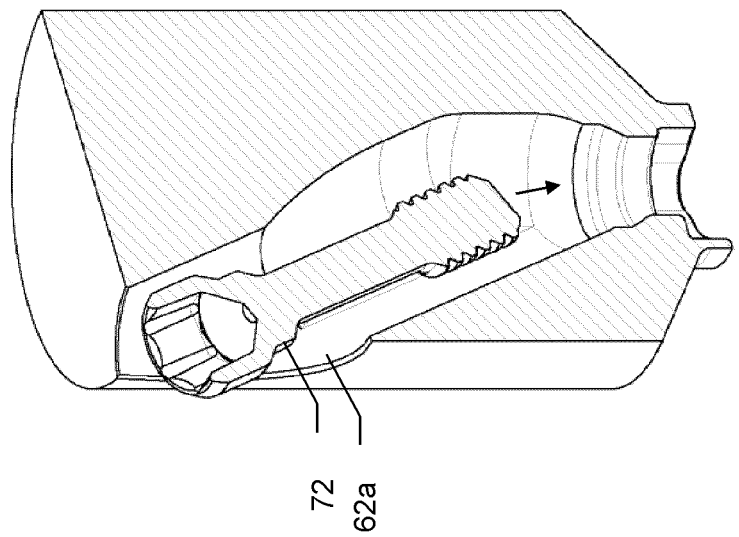
FIGS. 1a-1e show in sequence a method of attaching a dental component to a dental implant according to an embodiment of the present invention.
Figure 1A:
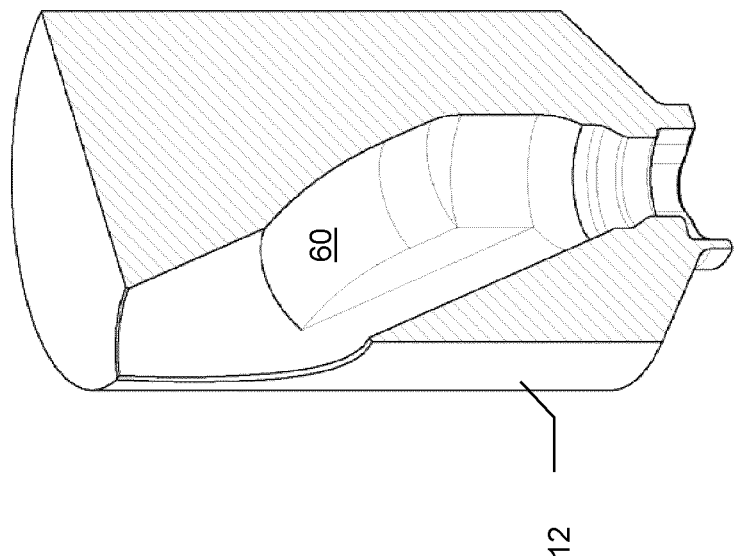
Figure 1E:
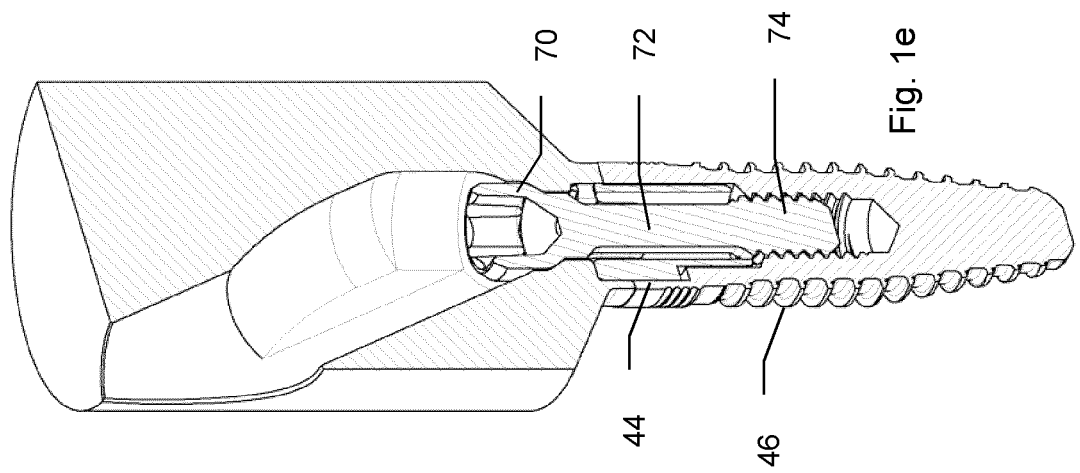
Figure 1D:
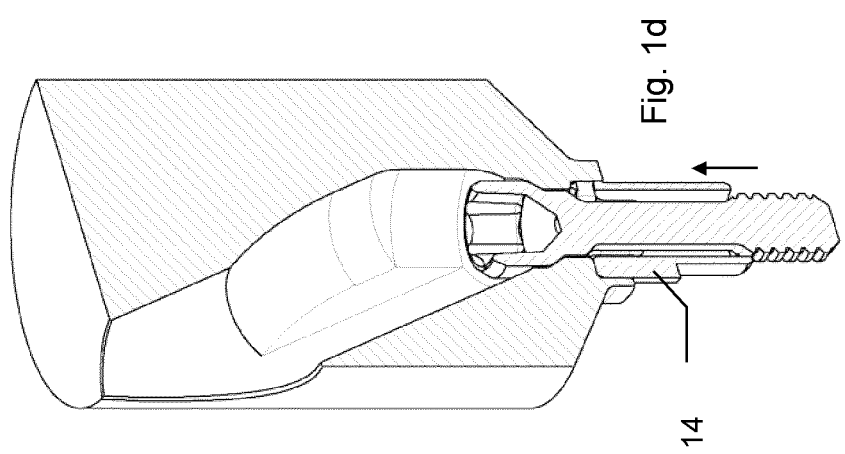
Figure 1C:
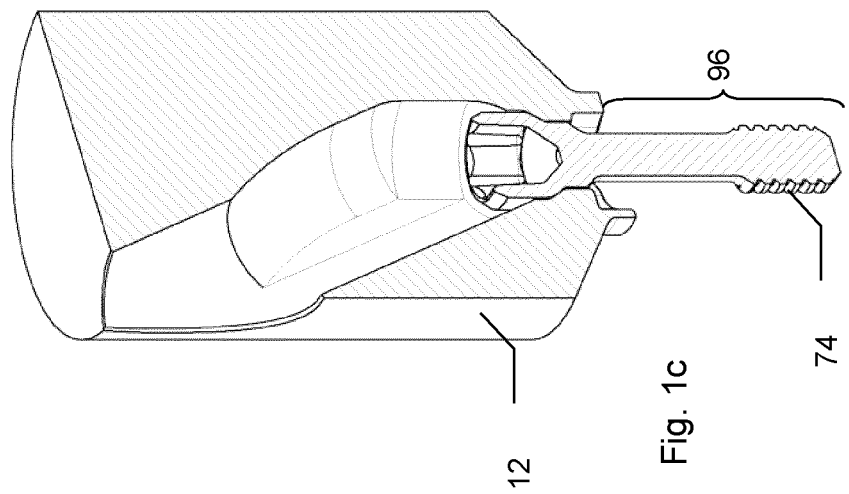

Then the screw 72 is inserted into the screw channel 60 through the first opening 62a (FIG. 1b). The screw 72 is passed through the screw channel 60 so that a portion 96 of the screw 72 opposite the head 70 protrudes through the second opening 62b at the apical end 64b of the screw channel (FIG. 1c). Since the metal adapter 14 is not yet attached to the component body 12, the screw 72 does not have to be aligned with the longitudinal axis 92b at the apical end 64b before the screw 72 is brought through the second opening 62b. This allows for a narrow angled screw channel 60. As the portion 96 of the screw 72 protrudes through the second opening 62b, the head 70 of the screw is conveniently seated on the screw seat 68.

Then, the metal adapter 14 is attached to the component body 12 (FIG. 1d), preferably from below. This takes part outside a patient's mouth.

Finally, the dental component 10 (i.e. the component body 12 with the attached metal adapter 14), together with the screw already inserted into the screw channel 60, is applied to the dental implant 46, and fixed to the dental implant 46 using the screw 72 (FIG. 5e).

The dental implant to which the dental component 10 is attached may be anchored in a jaw bone of the patient, or it may be arranged in a physical model. In the latter case, the dental implant may be a replica or implant analog.

The person skilled in the art realizes that the present invention by no means is limited to the preferred embodiments described above. On the contrary, many modifications and variations are possible within the scope of the appended claims.

The invention claimed is:

1. A dental component for attachment to a dental implant, the dental component comprising:
   a screw having a length and having a head at one end of the screw, the head having a maximum cross-sectional dimension perpendicular to a longitudinal axis of the screw,
   a component body, wherein the component body is made of ceramic and comprises a screw channel passing through the component body and forming a first opening at a first end and a second opening at an apical end, and a screw seat proximal to the apical end of the screw channel for seating the head of the screw for fixation of the dental component to the dental implant, wherein a central longitudinal axis of the screw channel at the first end does not match a central longitudinal axis of the screw channel at the apical end and wherein a distance, along the central longitudinal axis of the screw channel at the apical end, between the second opening and an inner surface of the screw channel is less than the length of the screw, and wherein the first opening has a minimum cross-sectional dimension perpendicular to the central longitudinal axis of the screw channel at the first end, and wherein the maximum cross-sectional dimension perpendicular to the longitudinal axis of the screw of the head is smaller than the minimum cross-sectional dimension perpendicular to the central longitudinal axis of the screw channel at the first end and wherein a diameter of the screw channel varies from the first opening to the screw seat; and an adapter that is made of metal and is removably attachable to the component body, wherein the adapter comprises a bore passing through the adapter and forming a coronal opening and an apical opening.

2. The dental component according to claim 1, wherein the bore is aligned with the screw channel at the second opening when the adapter is attached to the component body.

3. The dental component according to claim 1, wherein the adapter comprises a conical connection interface for attachment to the dental implant, the conical connection interface comprising an external conical shape tapering towards an apical end of the adapter, and an external indexed portion provided apically of the external conical shape adjacent to the apical end of the adapter.

4. The dental component according to claim 1, wherein the adapter comprises at least one flexible arm with a protrusion adapted to press against a side wall or snap into any corresponding undercut of the component body for securing the adapter to the component body in the coronal-apical direction.

5. The dental component according to claim 1, wherein the adapter includes at least one convex lobe adapted to abut against at least one corresponding concave recess in the component body for preventing rotation between the component body and the adapter.

6. The dental component according to claim 5, wherein said at least one convex lobe extends apically of an apical end of the component body when the adapter is attached to the component body.

7. The dental component according to claim 1, wherein the component body is adapted to support a dental restoration.

8. The dental component according to claim 1, wherein the component body is a crown, a bridge, or a full-contour part.

9. The dental component according to claim 1, wherein the screw is sized such that a threaded portion of the screw extends through the second opening when the head of the screw is proximal of the screw seat.

* * * * *